United States Patent
Chow

(10) Patent No.: US 9,747,431 B2
(45) Date of Patent: *Aug. 29, 2017

(54) MULTIPLE USER ACCOUNTS FOR MANAGING STORED INFORMATION IN AN IMPLANTABLE MEDICAL DEVICE SYSTEM

(71) Applicant: Medtronic, Inc., Minneapolis, MN (US)

(72) Inventor: Theodore Chow, Saratoga, CA (US)

(73) Assignee: Medtronic, Inc., Minneapolis, MN (US)

( * ) Notice: Subject to any disclaimer, the term of this patent is extended or adjusted under 35 U.S.C. 154(b) by 68 days.

This patent is subject to a terminal disclaimer.

(21) Appl. No.: 14/665,824

(22) Filed: Mar. 23, 2015

(65) Prior Publication Data
US 2015/0193612 A1  Jul. 9, 2015

Related U.S. Application Data

(63) Continuation of application No. 12/493,889, filed on Jun. 29, 2009, now Pat. No. 8,990,924.

(Continued)

(51) Int. Cl.
*G06F 21/00* (2013.01)
*G06F 21/34* (2013.01)
(Continued)

(52) U.S. Cl.
CPC ......... *G06F 21/34* (2013.01); *A61N 1/37247* (2013.01); *A61N 1/37252* (2013.01);
(Continued)

(58) Field of Classification Search
CPC .......... G06F 21/34; G06F 21/31; G06F 21/30; G06F 21/44; G06F 21/00; G06F 19/30;
(Continued)

(56) References Cited

U.S. PATENT DOCUMENTS 4,432,360 A * 2/1984 Mumford ........... A61N 1/37247
607/30
6,480,745 B2 11/2002 Nelson et al.
(Continued)

FOREIGN PATENT DOCUMENTS

WO       0149369 A1      7/2001
WO    WO 0149369 A1 *   7/2001  ............. A61B 5/117
WO    2005101279 A2    10/2005

OTHER PUBLICATIONS

International Search Report and Written Opinion for corresponding PCT Application Serial No. PCT/US2009/054932 mailed Dec. 11, 2009 (11 pages).

(Continued)

*Primary Examiner* — William Goodchild
(74) *Attorney, Agent, or Firm* — Shumaker & Sieffert, P.A.

(57) ABSTRACT

Techniques for managing stored information in an implantable medical device system using multiple user accounts are described. An implantable medical device system may provide a general user account and a set of authenticable user accounts. In some examples, the general user account does not require a user of a programmer in an implantable medical device system to enter user identity information to manage information stored in the implantable medical device system. The general user account may be permitted to perform a subset of actions available to an authenticable user account. In some examples, an authenticable user account may rollback changes made to the stored information by the general user account. An authenticable user account may also be able to synchronize changes made to the stored information across all or some of the user accounts.

20 Claims, 9 Drawing Sheets

Related U.S. Application Data

(60) Provisional application No. 61/190,207, filed on Aug. 27, 2008.

(51) Int. Cl.
*A61N 1/372* (2006.01)
*G06F 19/00* (2011.01)
*G06F 21/31* (2013.01)
*A61N 1/39* (2006.01)

(52) U.S. Cl.
CPC ....... *A61N 1/37264* (2013.01); *A61N 1/3956* (2013.01); *G06F 19/3412* (2013.01); *G06F 21/31* (2013.01)

(58) Field of Classification Search
CPC .. G06F 19/34; G06F 19/3406; G06F 19/3412; A61N 1/37247; A61N 1/37252; A61N 1/37264; A61N 1/3956; A61N 1/00; A61N 1/18; A61N 1/32; A61N 1/36; A61N 1/372; A61N 1/37211; A61N 1/37235
USPC .......................................................... 726/17
See application file for complete search history.

(56) References Cited

U.S. PATENT DOCUMENTS

| | | | |
|---|---|---|---|
| 6,497,655 B1 | 12/2002 | Linberg et al. | |
| 6,735,478 B1 | 5/2004 | Snell | |
| 6,880,085 B1 | 4/2005 | Balczewski et al. | |
| 6,961,448 B2 | 11/2005 | Nichols et al. | |
| 6,961,617 B1 | 11/2005 | Snell | |
| 7,188,151 B2 | 3/2007 | Kumar et al. | |
| 7,236,833 B2 | 6/2007 | Graindorge et al. | |
| 7,324,949 B2 | 1/2008 | Bristol | |
| 8,577,967 B1 | 11/2013 | Chavez et al. | |
| 2002/0095499 A1 | 7/2002 | Barnett et al. | |
| 2002/0138155 A1 | 9/2002 | Bristol | |
| 2005/0283198 A1* | 12/2005 | Haubrich | G06F 19/3418 607/30 |
| 2006/0017575 A1 | 1/2006 | McAdams | |
| 2006/0017576 A1 | 1/2006 | Gordon et al. | |
| 2006/0179135 A1* | 8/2006 | Murai | H04W 28/18 709/223 |
| 2006/0247709 A1 | 11/2006 | Gottesman et al. | |
| 2006/0294011 A1* | 12/2006 | Smith | G06Q 50/16 705/51 |
| 2007/0078497 A1 | 4/2007 | Vandanacker | |
| 2007/0179567 A1 | 8/2007 | Gennaro | |
| 2007/0251988 A1* | 11/2007 | Ahsan | G06Q 10/06 235/375 |
| 2008/0065236 A1 | 3/2008 | Bristol | |
| 2008/0178050 A1* | 7/2008 | Kern | G06F 11/1666 714/54 |

OTHER PUBLICATIONS

Response to Written Opinion from corresponding PCT Application Serial No. PCT/US2009/054932 filed on Jun. 22, 2010 (16 pages).
International Preliminary Report on Patentability from corresponding PCT Application Serial No. PCT/US2009/054932 dated Jul. 26, 2010 (12 pages).
European Office Action from European application No. 09 791 901.3-1652, dated Jan. 22, 2014, 5 pp.
Response to European Office Action dated Jan. 22, 2014, from European Patent Application No. 09791901.3, filed Jun. 2, 2014, 7 pp.
Prosecution History from U.S. Appl. No. 12/493,889, dated Sep. 29, 2011 through Feb. 11, 2015, 131 pp.

* cited by examiner

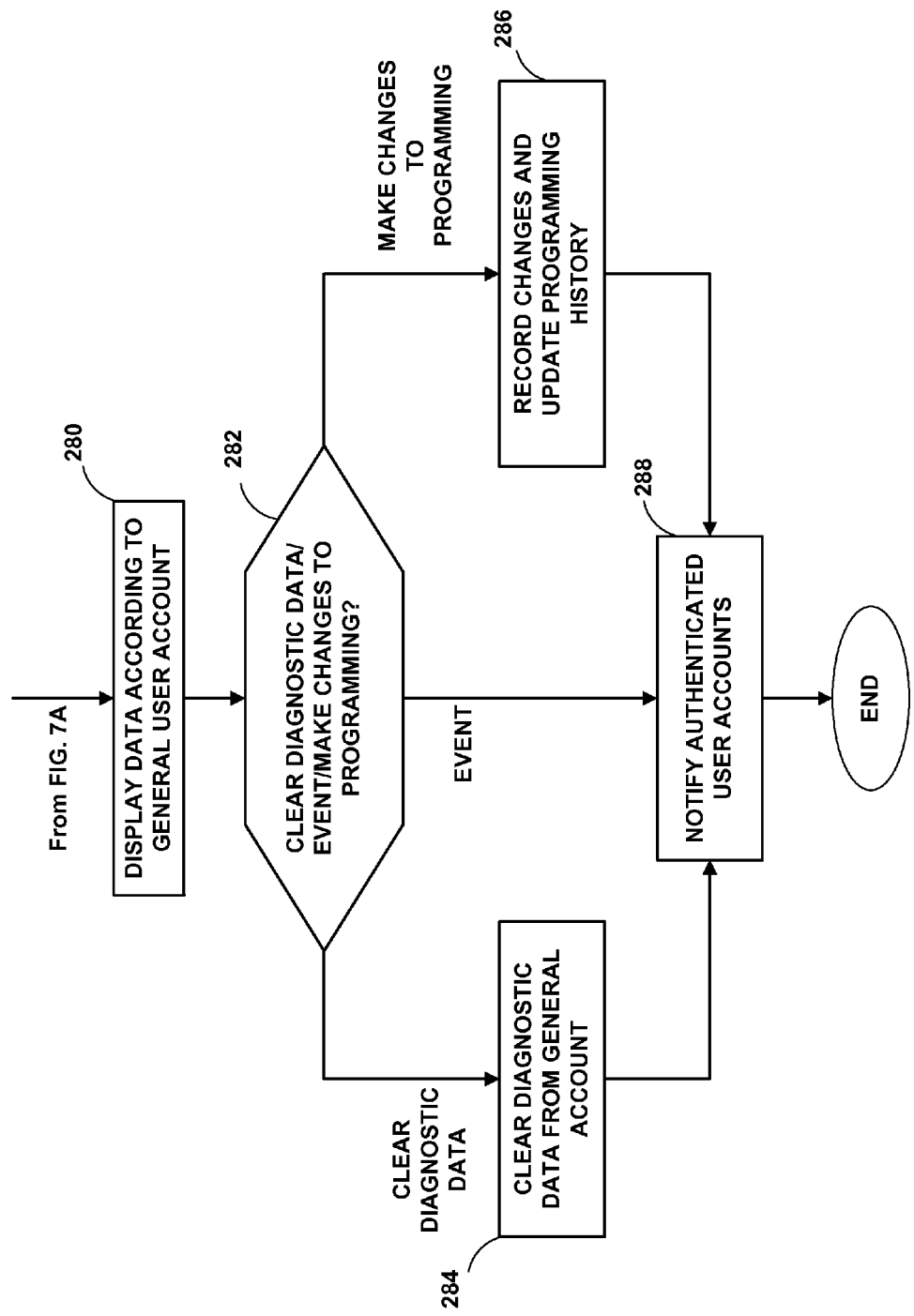

MULTIPLE USER ACCOUNTS FOR MANAGING STORED INFORMATION IN AN IMPLANTABLE MEDICAL DEVICE SYSTEM

This application is a continuation of U.S. application Ser. No. 12/493,889, filed Jun. 29, 2009, which claims the benefit of U.S. Provisional Application No. 61/190,207, filed Aug. 27, 2008, the entire contents of both are incorporated herein by reference.

TECHNICAL FIELD

This disclosure relates to medical device systems and, more particularly, systems including implantable medical devices.

BACKGROUND

A variety of implantable medical devices for delivering a therapy and/or monitoring a physiological condition have been clinically implanted or proposed for clinical implantation in patients. Implantable medical devices may deliver electrical stimulation or fluid therapy to and/or monitor conditions associated with the heart, muscle, nerve, brain, stomach or other organs or tissue. Examples of implantable medical devices include cardiac pacemakers, cardioverters, defibrillators, or devices combining two or more of these functions, which typically also monitor the electrical activity of the heart, and may also monitor other physiological parameters, such as activity, posture, or various vascular or cardiac flows or pressures.

Implantable medical devices may store a variety of information. For example, implantable medical devices may store information regarding the current operating parameters for the device that control the therapy delivery and patient monitoring functionality of the device, or changes made to these parameters over time. As another example, implantable medical devices may store diagnostic data, which may include monitored physiological parameters of the patient, or parameters of the device. The diagnostic data may also include information regarding events, such as the occurrence of a clinically significant patient event or the delivery of a responsive therapy. For example, an implantable medical device may store information regarding the occurrence of a tachyarrhythmia, e.g., including a corresponding electrogram and marker channel, and the delivery of a responsive therapy, such as a fibrillation pulse.

Implantable medical devices typically interact with a programmer that allows a user to manage information stored on the implantable medical device, e.g., change operation parameters or view information collected by the device. Various types of individuals may use a programmer including physicians, technicians, surgeons, electrophysiologists, or other clinicians. Conventional programmers and implantable medical devices provide any such user complete access and control over the stored information.

SUMMARY

Changes made to the information stored by an implantable medical device by one clinician using a programmer may not be obvious or apparent to another clinician who later accesses the implantable medical device using the same programmer or a different programmer. For example, a primary following clinician for a patient may be unaware of changes to the stored information made by some other clinician, such as a clinician at an emergency department of a hospital to which the patient was admitted in the case of an emergency. The changes made by the other clinician may be intentional or accidental, and may include clearing information collected by the implantable medical device since the last time the primary clinician interrogate the implantable medical device. The incomplete information presented to the primary clinician may lead to difficulty in diagnosing a medical problem by the primary clinician, as well as impaired medical treatment of the patient.

For example, if a patient presents to an emergency department because an implantable medical device improperly delivered a defibrillation pulse in response to sinus tachycardia, a clinician in the emergency department may reprogram the implantable medical device to remove a ventricular tachycardia zone, which may stop the implantable medical device from inappropriately delivering defibrillation pulses in response to sinus tachycardia. The emergency department clinician may also clear the information regarding the incorrect ventricular tachycardia detections and delivery of defibrillation pulses from the memory of the implantable medical device. When the patient later visits his or her principle following clinician, the different clinician may notice the programming change, but not the ventricular tachycardia episode that was cleared. The principle following clinician may reprogram the ventricular tachycardia zone, and the implantable medical device may subsequently deliver an inappropriate defibrillation pulse.

As another example, a primary clinician may optimize the atrioventricular delay or other aspects of the timing of cardiac resynchronization therapy provided by an implantable medical device. Another clinician may accidentally change the optimized setting, causing the patient to not feel well. The patient may return to the primary clinician, but the primary clinician may not notice the changed setting, and misattribute the reason for the patient not feeling well.

As another example, a primary clinician may decide to treat recurrent ventricular tachycardia in a patient who has an implantable medical device with amiodarone. An emergency department clinician may clear information regarding a subsequent long run of ventricular tachycardia that caused admission of the patient to the emergency department from the implantable medical device memory following interrogation of the implantable medical device. During a subsequent follow up visit, the primary clinician may interpret the lack of ventricular tachycardia episodes in the implantable medical device memory as evidence that the amiodarone was successful, and not change the therapy provided to the patient to address the breakthrough of ventricular tachycardia while the patient was on amiodarone.

In general, this disclosure is directed to techniques for managing information stored in an implantable medical device system by using multiple user accounts. The techniques may include authenticating a user of an implantable medical device system as a general user or as one of a set of authenticable users. In some examples, the general user may perform a subset of the actions that may be performed by an authenticable user, such as only being able to clear information from the general user account. In some examples, in response to changes made to the stored information by a general user, the implantable medical device system notifies the set of authenticable users of the changes.

In some examples, an authenticable user may review changes made by the general user, e.g., to the operational parameters of the implantable medical device, and undo or rollback those changes. An authenticable user may also make programming changes or review a programming history of the implantable medical device system. Furthermore, an authenticable user may synchronize any changes made while managing the stored information across one or more of the set of authenticable user accounts and the general user account.

In some examples, the stored information may be stored in memory of an implantable medical device or in memory of a programmer device. The stored information may also span memories of both devices. The stored information may comprise operational parameters for controlling the implantable medical device or a history of such operational parameters. In addition, the stored information may include diagnostic data such as, such as physiological data of the patient and events, such as the occurrence of a symptomatic event or the delivery of a responsive therapy. Examples of diagnostic data also include diagnostics of the device, such as a percent of pacing, mode switching information, which may also be useful to diagnosing the patient, as well as battery voltage, lead impedance, or short R-R interval sensing.

In one example, a method comprises storing data of an implantable medical device and a set of user accounts in a memory, wherein the set of user accounts comprises a general user account and a set of one or more authenticable user accounts, determining whether a user of a programmer that communicates with the implantable medical device is a general user or an authenticable user, and accessing one of the general user account or the set of authenticable user accounts based on the determination. Each of the accounts includes respective access control information that specifies a respective subset of the data of the implantable medical device available and respective actions available for managing the data. The method further comprises controlling access and management of the data of the implantable medical device by the user according to the access control information of the accessed one of the accounts.

In another example, a system comprises an implantable medical device, a programmer that communicates with the implantable medical device, a memory, and a processor. The memory stores data of the implantable medical device and a set of user accounts, wherein the set of user accounts comprises a general user account and a set of one or more authenticable user accounts. The processor determines whether a user of the programmer is a general user or an authenticable user, accesses one of the general user account or the set of authenticable user accounts in the memory based on the determination, wherein the each of the accounts include respective access control information that specifies a respective subset of the data of the implantable medical device available and respective actions available for managing the data, and controls access and management of the data of the implantable medical device by the user according to the access control information of the accessed one of the accounts.

In another example, a system comprises means for storing data of an implantable medical device and a set of user accounts in a memory, wherein the set of user accounts comprises a general user account and a set of one or more authenticable user accounts, means for determining whether a user of a programmer that communicates with the implantable medical device is a general user or an authenticable user, means for accessing one of the general user account or the set of authenticable user accounts based on the determination, wherein the each of the accounts include respective access control information that specifies a respective subset of the data of the implantable medical device available and respective actions available for managing the data, and means for controlling access and management of the data of the implantable medical device by the user according to the access control information of the accessed one of the accounts.

In another example, a computer-readable storage medium comprises instructions that cause a programmable processor to access data of an implantable medical device and a set of user accounts, wherein the set of user accounts comprises a general user account and a set of one or more authenticable user accounts, determine whether a user of a programmer that communicates with the implantable medical device is a general user or an authenticable user, access one of the general user account or the set of authenticable user accounts based on the determination, wherein the each of the accounts include respective access control information that specifies a respective subset of the data of the implantable medical device available and respective actions available for managing the data, and control access and management of the data of the implantable medical device by the user according to the access control information of the accessed one of the accounts.

The details of one or more examples are set forth in the accompanying drawings and the description below. Other features, objects, and advantages of the disclosure will be apparent from the description and drawings, and from the claims.

BRIEF DESCRIPTION OF THE DRAWINGS

FIGS. 7A-7C are flow diagrams illustrating an example method for controlling the management of information stored by a medical device system using multiple user accounts.

DETAILED DESCRIPTION

Figure 1:
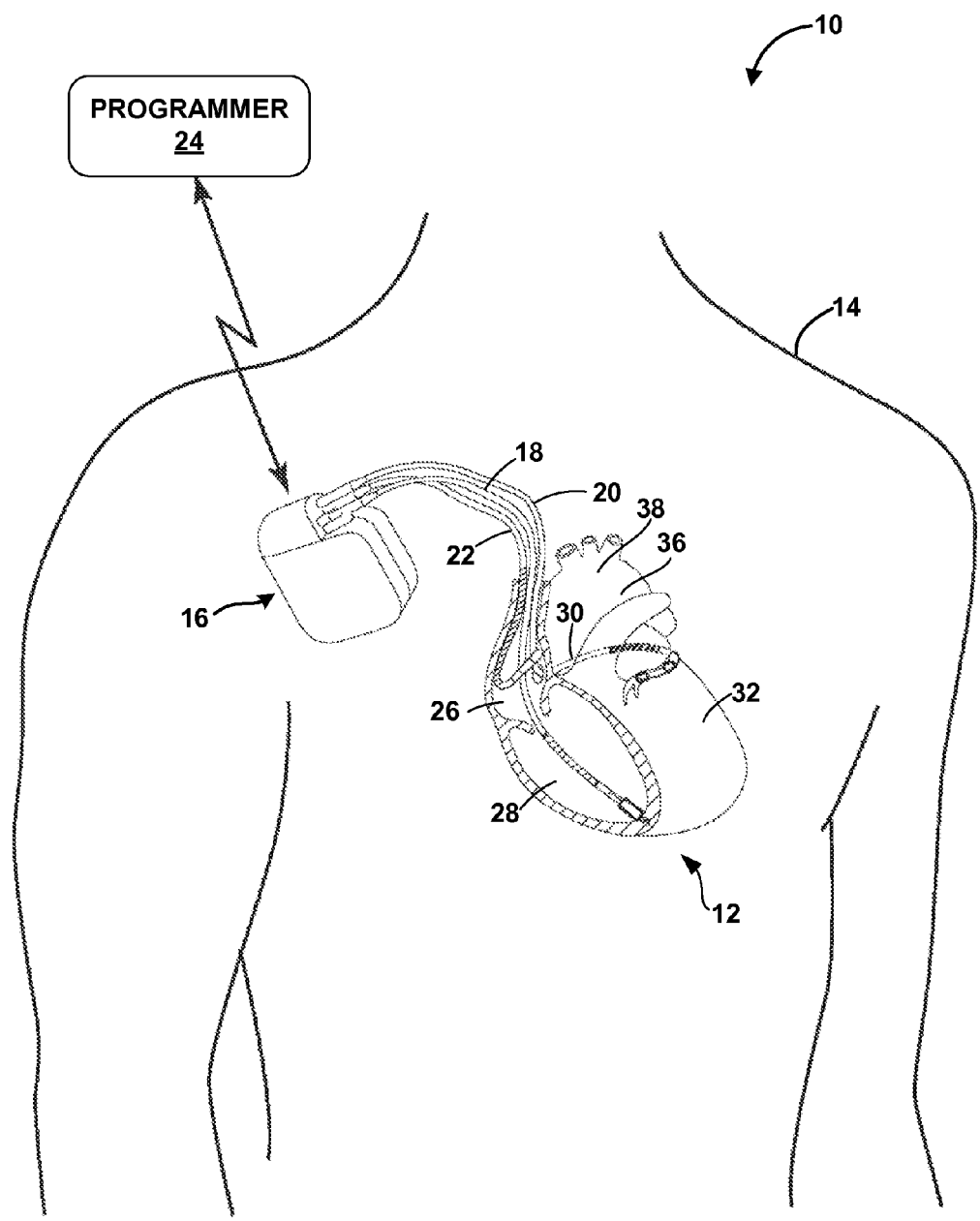
FIG. 1 is a conceptual drawing illustrating an example system that includes an implantable medical device (IMD) coupled to implantable medical leads and communicatively coupled to an external programmer.

FIG. 1 is a conceptual diagram illustrating an example implantable medical device (IMD) system 10. IMD system 10 includes an implantable medical device (IMD) 16. IMD system 10 also include an external programmer 24 communicatively coupled to IMD 16.

In the illustrated example, IMD 16 is a cardiac device that monitors and/or delivers therapy to heart 12. IMD 16 may provide pacemaker, cardioverter and/or defibrillator functionality, as examples. For example, IMD 16 may be an implantable pacemaker-cardioverter-defibrillator. However, the disclosure is not limited to examples in which an IMD is a cardiac device. In other examples, an IMD may comprise an implantable neurostimulator, implantable pump, implantable loop recorder, or any other implantable medical device that delivers therapy to and/or monitors a patient.

In the illustrated example, IMD 16 is coupled to leads 18, 20 and 22. Leads 18, 20 and 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12. The numbers, implant locations, and configurations of leads 18, 20 and 22 in FIG. 1 are merely examples.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., defibrillation pulses with increasing energy levels, until a fibrillation of heart 12 is stopped.

Programmer 24 may take the form of a handheld computing device, computer workstation, or networked computing device, as examples. Programmer 24 may include a user interface that presents information to and receives input from a user. A user, such as a physician, technician, surgeon, electrophysiologist, or other clinician, may interact with programmer 24 to retrieve physiological or other diagnostic information from IMD 16. A user may also interact with programmer 24 to program IMD 16, e.g., select values for operational parameters of the IMD 16.

For example, the user may use programmer 24 to retrieve diagnostic information from IMD 16 regarding the rhythm of heart 12, trends therein over time, or tachyarrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding delivery of therapy by IMD 16, such as the time and characteristics of delivered defibrillation or cardioversion pulses, information regarding times when IMD 16 automatically switched from one pacing mode to another, i.e., mode switching, and information regarding the degree to which the patient was paced, e.g., percent pacing, which may be significant for evaluating the efficacy of cardiac resynchronization therapy. As another example, the user may use the programmer 24 to retrieve information from IMD 16 regarding the performance or integrity of IMD 16 or other components of system 10, such as leads 18, 20 and 22, or a power source of IMD 16.

The user may use programmer 24 to program a therapy progression, select electrodes used to deliver defibrillation pulses, select waveforms for the defibrillation pulse, or select or configure a fibrillation detection algorithm for IMD 16. The user may also use the programmer 24 to program aspects of other therapies provided by IMD 16, such as cardioversion or pacing therapies. In some examples, a user may be required enter user identity information into the programmer 24 before being permitted to interact with the programmer 24 and the IMD 16. If the user elects not to enter user identity information, the user may only have the ability to perform a certain, reduced number of features the user would otherwise be able to perform.

IMD 16 and programmer 24 may communication via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
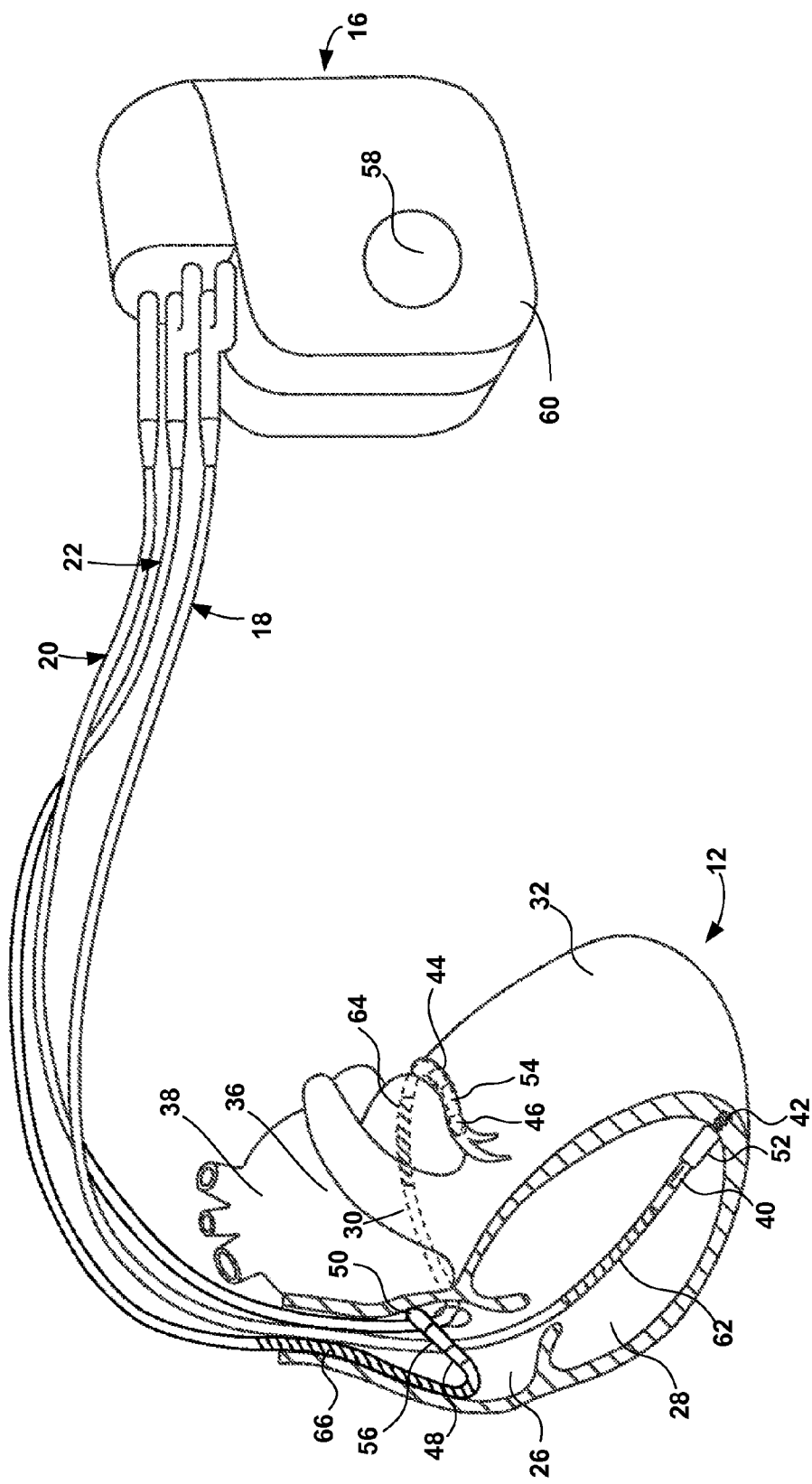
FIG. 2 is a conceptual drawing illustrating the example IMD and leads of FIG. 1 in conjunction with a heart.

FIG. 2 is a conceptual diagram illustrating IMD 16 and leads 18, 20, and 22 of system 10 in greater detail. Leads 18, 20 and 22 include conductors that are electrically coupled to a stimulation generator and an electrical sensing module (FIG. 3) within a housing 60 of IMD 16. The conductors are also coupled to electrodes on the leads.

Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. Leads 18, 20, 22 also include elongated electrodes 62, 64, 66, respectively, which may take the form of a coil. There are no electrodes located in left atrium 36, but other examples may include electrodes in left atrium 36. Furthermore, other examples may include electrodes in other locations, such as the aorta or a vena cava, or epicardial or extracardial electrodes proximate to any of the chambers or vessels described herein. Each of the electrodes 40, 42, 44, 46, 48, 50, 62, 64, and 66 may be electrically coupled to a respective conductor within the lead body of its associated lead 18, 20, 22, and thereby coupled to the stimulation generator and sensing module within housing 60 of IMD 16.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Housing electrode 58 is also coupled to one or both of the stimulation generator and sensing module within housing 60 of IMD 16.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58.

In some examples, IMD 16 delivers pacing pulses via bipolar combinations of electrodes 40, 42, 44, 46, 48 and 50 to produce depolarization of cardiac tissue of hear 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12.

Figure 3:
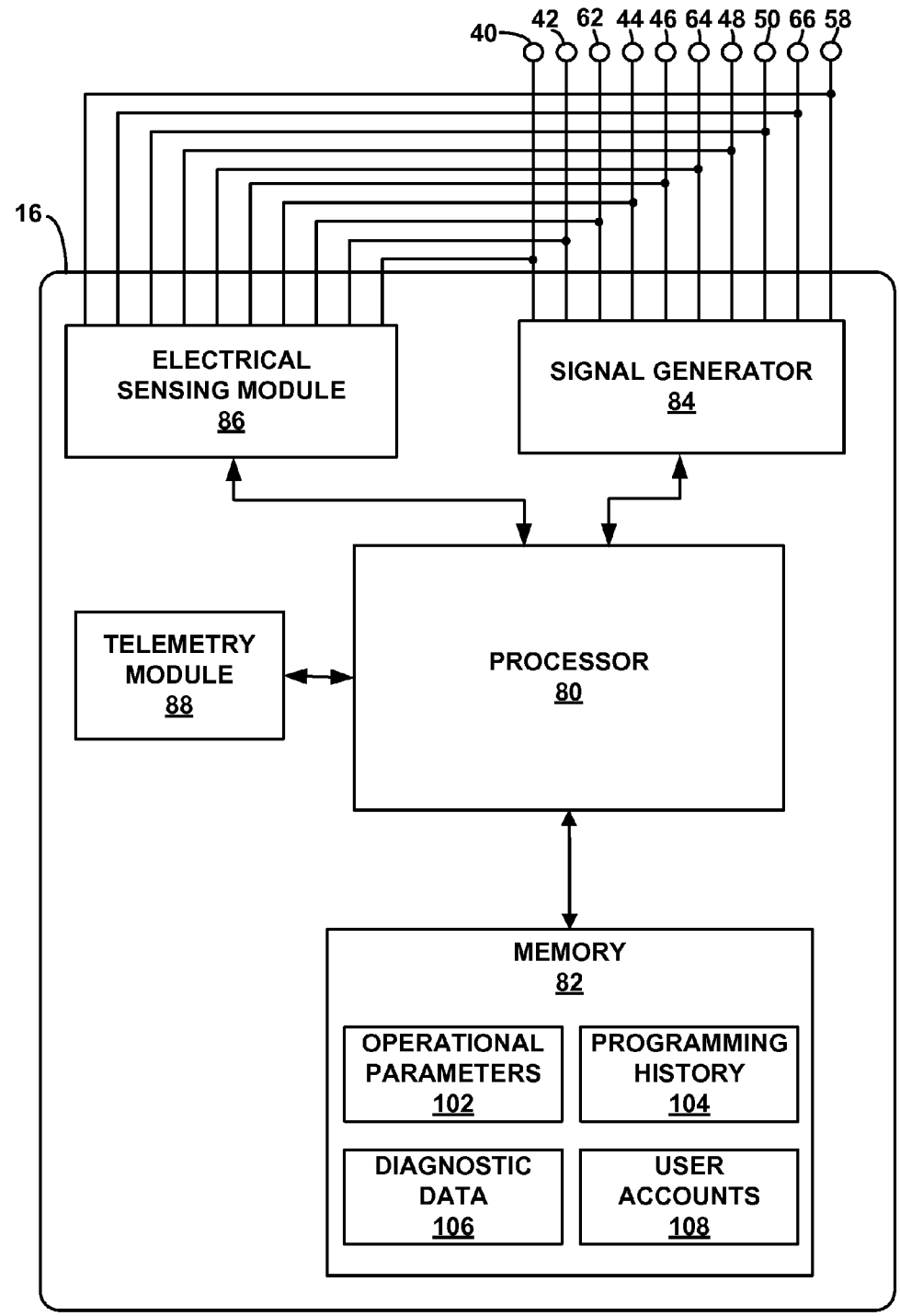
FIG. 3 is a functional block diagram illustrating an example configuration of the IMD of FIG. 1.

FIG. 3 is a functional block diagram illustrating one example configuration of IMD 16. In the illustrated example, IMD 16 includes a processor 80, memory 82, signal generator 84, electrical sensing module 86 and telemetry module 88. Memory 82 includes computer-readable instructions that, when executed by processor 80, cause IMD 16 and processor 80 to perform various functions attributed to IMD 16 and processor 80 herein. These computer-readable instructions may include operational parameters 102, sometimes referred to as a program or programs, that control the way the IMD 16 operates. Memory 82 may store a history of the operational parameters 102 used in controlling the IMD 16 at various times during the operation of IMD 16 in a programming history 104.

In addition, memory 82 may store any information sensed by any electrode or any combination of electrodes 40, 42, 44, 46, 48, 50, 62, 64 and 66, including information stored in the form of a cardiac electrogram (EGM), as diagnostic data 106. In some examples, IMD 16 comprises other sensors, such as a patient activity, motion and/or posture sensor, which may take the form of one or more accelerometers, a cardiac or vascular blood pressure sensor, a blood flow sensor, a blood oxygen sensor, or a respiration sensor. Memory 82 may store information regarding such physiological parameters of patient 14 monitorable by such sensors, e.g., values or trends of such physiological parameters, as diagnostic data 106. In some examples, memory 82 stores information regarding clinically significant events and/or therapeutic responses, such as tachyarrhythmias and responsive defibrillation pulses, as diagnostic data 106. Diagnostic data 106 may assist a user of programmer 24 in diagnosing and treating a patient 14. Memory 82 may also store user identity information corresponding to user accounts 108. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to operational parameters 102. For example, processor 80 may control stimulation generator 84 to generate electrical pulses with the amplitudes and pulse widths specified by operational parameters 102, and deliver the electrical pulses to the combination of electrodes 40, 42, 44, 46, 48, 50, 58, 62, 64 and 66 specified by operational parameters 102 (and thereby to a specified chamber of heart 14) with the electrode polarities specified by operational parameters 102. In some examples, processor 80 controls delivery of pacing pulses in response to a sensed depolarization and/or expiration of a timer according to any of a variety of known single or multiple chamber pacing modes as specified by operational parameters 102, and controls delivery of pacing, cardioversion and defibrillation pulses in response to a detected tachyarrhythmia in accordance with parameters and/or a therapy progression specified by operational parameters 102. In some examples, processor 80 automatically switches pacing modes in response to a sensed event, and information regarding such mode switching may be stored as diagnostic data 106.

Signal generator 84 is electrically coupled to electrodes 40, 42, 44, 46, 48, 50, 58, 62, 64 and 66, e.g., via conductors of the respective lead 18, 20, 22 or, in the case of housing electrode 58, via an electrical conductor disposed within housing 60 of IMD 16. Signal generator 84 is configured to generate and deliver electrical stimulation therapy to heart 12. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12. Electrical sensing module 86 may also include a switch module to select which of the available electrodes are used to sense the heart activity. In some examples, electrical sensing module 86 includes multiple detection channels, each of which may be selectively coupled to respective combinations of electrodes 40, 42, 44, 46, 48, 50, 58, 62, 64 or 66 to detect electrical activity of a particular chamber of heart 12. Each detection channel may comprise an amplifier that outputs an indication to processor 80 in response to detection of an event, such as a depolarization, in the respective chamber of heart 12.

Processor 80 controls delivery of stimulation by signal generator 84 based on the indications received from electrical sensing module 86, or the absence of such indications, as is known in the art. Processor 80 may also detect tachyarrhythmias based on the rate of such indications, as is known in the art. Processor 80 may store information regarding heart rate, R-R intervals, and other information derived from the indications from sensing module 86, in memory 82 as diagnostic data 106.

In some examples, sensing module 86 comprises a channel that provides a signal sensed via a combination of the electrodes to an analog-to-digital converter (not shown), which provides a digitized signal to processor 80. Processor 80 may analyze the signal, e.g., for tachyarrhythmia detection, and/or store the signal in memory 82 as an EGM. In some examples, EGMs are stored with a marker channel that indicates time correlated events, such as depolarizations detected by sensing module 86, detection of a tachyarrhythmia, and delivery of a responsive therapy, e.g., defibrillation pulse. EGMs and marker channels may be stored as diagnostic data 106 in memory 82. Operational parameters 102 may include information specifying the amplification, blanking or filtering of channels of sensing module 86, as well as the storage of diagnostic data 106 by processor 80.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide data to be uplinked to programmer 24 and receive data from programmer 24 via telemetry module 88.

Figure 4:
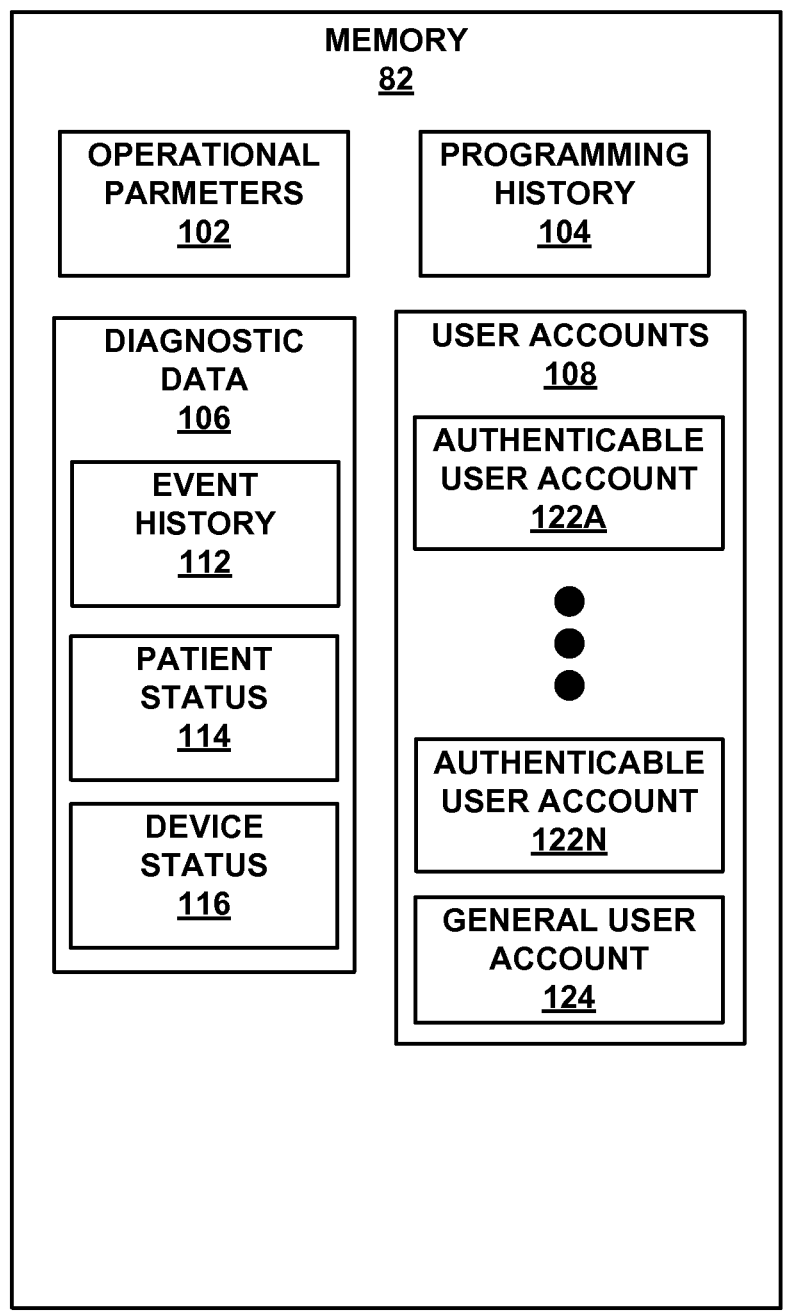
FIG. 4 is a block diagram further illustrating information stored in a memory of the IMD shown in FIG. 3.

FIG. 4 is a block diagram further illustrating memory 82. As illustrated by FIG. 4, diagnostic data 106 may comprise an event history 112, patient status information 114, and device status information 116. Event history 112, for example, is comprised of various types of events such as ventricular tachycardia (VT) episodes, ventricular fibrillation (VF) episodes, atrial fibrillation (AF) episodes, decompensation events, pacing mode switches by IMD 16, or responsive therapies delivered by IMD 16. In an example in which an IMD comprises an implantable pump, event history 112 may include automatic delivery of bolus by IMD 16 or patient 14 initiated delivery of bolus. Patient status information 114 may comprise any of various types of indicators of patient status, such as physiological parameter values or trends, heart failure indices, patient activity history, or heart rate variability, which aid in evaluating the health status of patient 14. Device status information 116 may comprise indicators of the performance of IMD 16 or other components of system 10, such as leads 18, 20 and 22, or a power source of IMD 16. Examples of device status information 116 include lead impedance measurements or trends, percent biventricular pacing, or numbers or frequencies of detected short R-R intervals, which may be nonphysiologic.

User accounts 108 of memory 82 may include a general user account 124 which may not require a user of programmer 24 to enter user identity information before permitting the user to interact with programmer 24 and IMD 16. User accounts 108 also include a set of authenticable user accounts, 122A to 122N. Processor 80 may execute computer-readable instructions stored in memory 82 which cause the processor to receive user identity information from programmer 24, compare the user identity information to user accounts 108 stored in memory 82, and generate access control information. The user identity information may comprise, for example, a user name and password. The access control information specifies actions available to the user for managing any or all of the information stored in memory 82. The access control information may also specify how the user of the programmer 24 is permitted to interact with the programmer 24 and/or IMD 16.

The access control information may be applied by processor 80 when determining what information to provide programmer 24 via telemetry module 88 or how respond to commands from programmer 24. In some examples, processor 80 provides the access control information to programmer 24 via telemetry module 88. Programmer 24 may apply the access control information received from IMD 16 to control the actions made available to the user of programmer for interacting with IMD 16 and managing the information stored in memory 82 of IMD 16.

In one example, the user of programmer 24 may elect to enter user identity information corresponding to general user account 124. If the user elects not to enter user identity information, programmer 24 behaves as if the user entered user identity information corresponding to general user account 124. In either case, the user is considered an unauthenticated user. Processor 80 generates access control information corresponding to general user account 124 which specifies actions available to the unauthenticated user for managing stored information.

When processor 80 and/or programmer 24 applies this access control information, for example, the unauthenticated user is able perform various actions including clearing diagnostic data 106 from general user account 124. After the unauthenticated user clears diagnostic data 106 form general user account 124, diagnostic data 106 is not cleared from memory 82 and is still viewable by one or more of the set of authenticable user accounts 122A to 122N. In other examples, the unauthenticated user is permitted to change operational parameters 102 to alter the therapy delivered by IMD 16, and processor 80 may then update programming history 104 to reflect the changes made to operational parameters 102. The unauthenticated user may also view programming history 104. However, the unauthenticated user may not be permitted to synchronize programming changes across the set of authenticable user accounts 122A to 122N or clear programming history 104 from memory 82.

After the unauthenticated user performs any action, such as changing operational parameters 102, a notification may be sent to one or more of the set of authenticable user accounts 122A to 122N. Notification of the authenticable user or users may comprise storing an indication that the data was cleared in the account 122, or by communication with a server 204 or computing device 210 via a network 202. As examples, the authenticable user may receive the notification via the user interface 144 of programmer 24 the next time the authenticable user accesses the programmer 24, via an email or web account, via a cellular phone or personal digital assistant, or by fax.

In another example, the user of programmer 24 elects to enter user identity information and the user identity information does not match the user identity information stored in any authenticable user account 122A to 122N. In this example, the user is not permitted to interact with programmer 24 or IMD 16 through an authenticable user account. However, the user may be permitted to interact with programmer 24 and IMD 16 through general user account 124 as described above.

In another example, the user of programmer 24 enters user identity information and the user identity information matches the user identity information stored in one of the set of authenticable user accounts 122A to 122N. Once processor 80 executes computer-readable instructions which cause processor 80 to match the user identity information with an authenticable user account, the user is considered an authenticated user. The set of authenticable user accounts 122A to 122N may have the same or different access control information associated with each individual authenticable user account. Processor 80 generates access control information corresponding to the matching authenticable user account. When processor 80 and/or programmer 24 applies this access control information, for example, the authenticated user may be permitted to perform such actions as clearing event history 112 from being viewable by general user account 124 or the user's authenticable user account. In other examples, the authenticated user may be permitted to clear event history 112 from memory 82 such that it is not viewable by general user account 124 or by any of the set of authenticable user accounts 122A to 122N.

In other examples, the authenticated user is permitted to make programming changes to operational parameters 102 and synchronize the programming changes across general user account 124 and one or more of the set of authenticable user accounts 122A to 122N. Processor 80 updates programming history 104 to reflect the programming changes made to operational parameters 102.

In further examples, processor 80 and/or programmer 24 applying the access control information results in the authenticated user being permitted to review the changes made by an unauthenticated user since the last time the authenticated user interrogated programmer 24 or IMD 16. For example, the authenticated user may view changes to operational parameters 102 in programming history 104. After reviewing the changes, the authenticated user may synchronize the changes across all user accounts 108. If the authenticated user does not approve of the changes, the authenticated user may elect to rollback the changes such that programmer 24 and IMD 16 are reset to the state prior to when the unauthenticated user made the changes. The authenticated user may make changes to operational parameters 102, and clear diagnostic data 106 or any portion of diagnostic data 106 from memory 82.

In some examples, the authenticated user is permitted to program the access control information corresponding to the general user account 124 to control which device features an unauthenticated user may adjust, clear or otherwise program. For example, the authenticated user may program the access control information corresponding to the general user account 124 such that when processor 80 and/or programmer 24 applies the access control information to an unauthenticated user, the unauthenticated user is not permitted to change operational parameters 102 to alter the therapy delivered by IMD 16 or clear diagnostic data 106 from general user account 124.

In another example, the authenticated user is permitted to program IMD 16 and/or programmer 24 to control what actions taken by an unauthenticated user generate a notification for one or more of the set of authenticated user accounts as described above. For example, the authenticated user may program IMD 16 to generate a notification any time an unauthenticated user makes changes to the operational parameters 102, but not generate a notification when an unauthenticated user clears the diagnostic data 106. The authenticated user may also be permitted to select what type or types of notification are provided for each of a plurality of particular actions by the unauthenticated user.

In addition to the notification to the authenticated user, in some examples, the authenticated user may select or enter an alert or message to be provided to any unauthenticated user in response to actions of the unauthenticated user when interacting with programmer 24 or IMD 16. The alert or message, such as a text message on a display of programmer 24, may be provided by programmer 24 in response to any interaction with programmer 24, or certain actions of the unauthenticated user, such as changing operation parameters 102 or clearing diagnostic data 106. The authenticated user may select what type or types of alerts or messages are provided to the unauthenticated user for each of a plurality of particular actions by the unauthenticated user.

As described above, an unauthenticated user may clear data from programming history 104 a diagnostic data 106 for the general user account 124, but not for one or more authenticable user accounts 122. An authenticable user may clear data from programming history 104 a diagnostic data 106 for that user's account 122, as well as the general user account 124, and in some cases for other authenticable user accounts 122. Clearing data herein may refer to changing a flag or other indication in an account 122 or 124 such that the user or users associated with the account are no longer able to access the data, rather than deleting the data from memory 142. In some examples, however, an authenticable user may clear programming history 104 and diagnostic data 106 such that it is deleted from memory 82.

It is contemplated and understood that when processor 80 and/or programmer 24 applies access control information, the user interacting with programmer 24 and IMD 16 through general user account 124 or one of the set of authenticable user accounts 122A to 122N may be restricted from managing operational parameters 102, programming history 104, diagnostic data 106 or user accounts 108 in many other ways and in different combinations of ways in addition to the examples described above.

Figure 5:
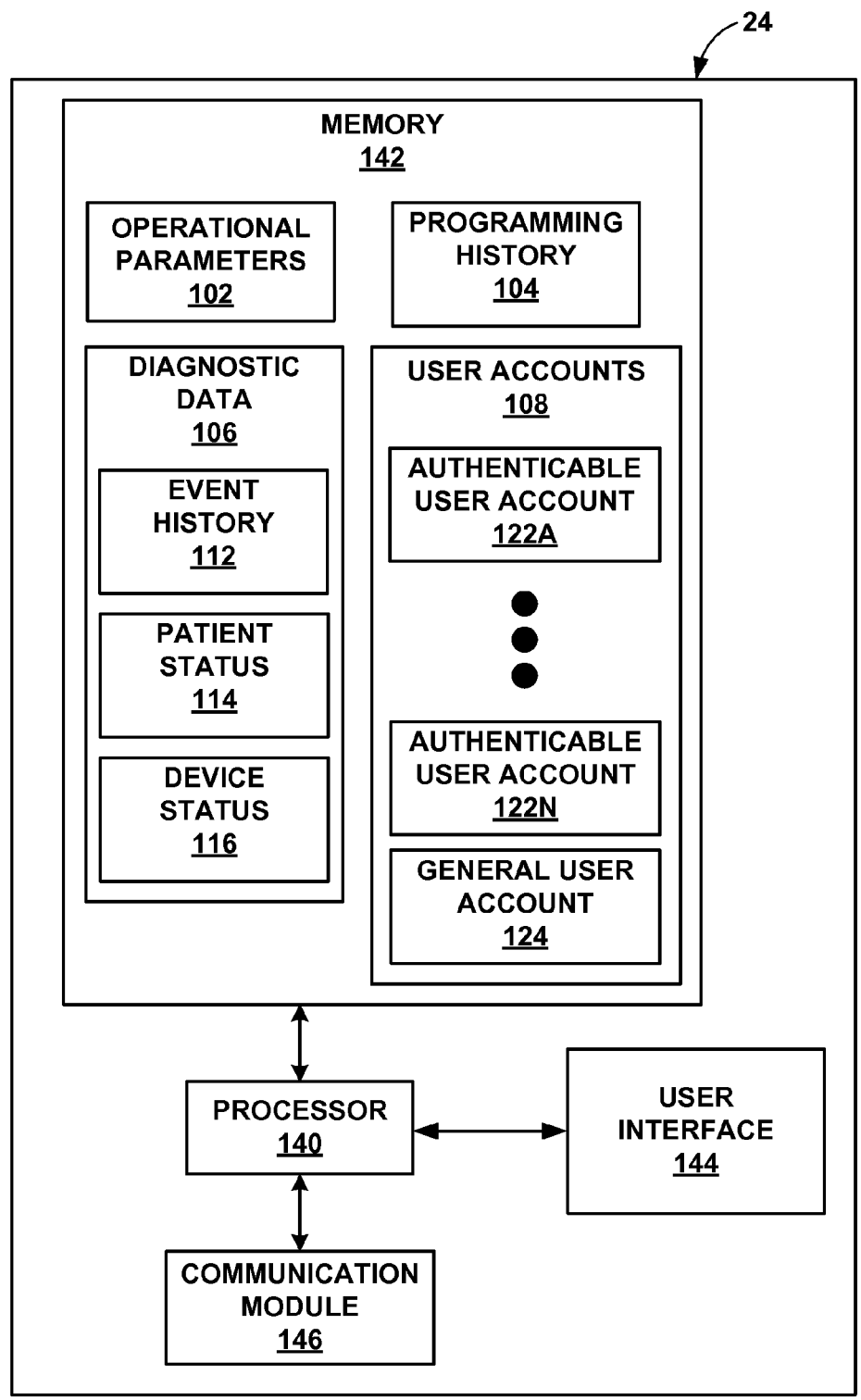
FIG. 5 is a block diagram illustrating an example configuration of the external programmer shown in FIG. 1.

FIG. 5 is a functional block diagram illustrating an example configuration of programmer 24. In general, programmer 24 comprises a computing device. In the example shown in FIG. 5, programmer 24 includes a processor 140, memory 142, user interface 144 and communication module 146. Programmer 24 may comprise a dedicated hardware device with dedicated software for programming of IMD 16. Alternatively, programmer 24 may comprise an off-the-shelf computing device running an application that enables programmer 24 to program IMD 16. For example, programmer 24 may comprise a workstation computer, a laptop computer, a hand-held device such as a personal digital assistant (PDA), a cellular phone or smart phone, or other devices.

A clinician or other user interacts with programmer 24 via user interface 144, which may include a display to present a graphical user interface to a user, and a keypad, mouse, light pen, stylus, microphone for voice recognition, or other mechanism(s) for receiving input from a user. In some examples, processor 140 retrieves an operational parameters 102, programming history 104, and diagnostic data 106 from IMD via communication module 146, and controls user interface 144 to present graphical and/or textual representations of the data.

Processor 140 can take the form of one or more microprocessors, DSPs, ASICs, FPGAs, programmable logic circuitry, or the like, and the functions attributed to processor 140 herein may be embodied as hardware, firmware, software or any combination thereof. Memory 142 may store instructions that cause processor 140 to provide the functionality ascribed to programmer 24 herein, and information used by processor 140 to provide the functionality ascribed to programmer 24 herein. Memory 142 may include any fixed or removable magnetic, optical, or electrical media, such as RAM, ROM, CD-ROM, hard or floppy magnetic disks, EEPROM, or the like. Processor 140 may include any one or more of a microprocessor, a controller, a digital signal processor (DSP), an application specific integrated circuit (ASIC), a field-programmable gate array (FPGA), or equivalent discrete or analog logic circuitry.

Memory 142 may store operational parameters 102, programming history 104, diagnostic data 106, and user accounts 108 retrieved from IMD 16. Any combination or portion of operational parameters 102, programming history 104, diagnostic data 106 and user accounts 108 may be stored in memory 82 of IMD 16, memory 142 of programmer 24, or both.

Programmer 24 may communicate wirelessly with IMD 16, such as by using RF communication or proximal inductive interaction. This wireless communication is possible through the use of communication module 146, which may be coupled to an internal antenna or an external antenna (not shown). Communication module 142 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16. An example of such an arrangement is discussed with respect to FIG. 6.

Processor 140 of programmer 24 may generate and apply access control information as described with respect to processor 80 of IMD 16. Accordingly, in one example, programmer 24 interrogates IMD 16 and retrieves user identity information corresponding to user accounts 108 of IMD 16 and stores the information in memory 142. Processor 140 compares user identity information entered by the user and received via user interface 144 to the user identity information stored in the set of authenticable user accounts 122A to 122N and to the user identity information stored in general user account 124. If the entered user identity information matches one of the set of authenticable user accounts, the user is an authenticated user. If the user identity information matches general user account 124, the user is an unauthenticated user. Again, in some examples, the user is allowed to interact with programmer 24 and IMD 16 as an unauthenticated user without entering any user identity information, e.g., interaction as a general user is a default state of programmer 24 and/or IMD 16. In another example, programmer 24 stores user accounts 108 in memory 142 and processor 140 performs the comparison described above without interrogating IMD 16. In another example, programmer 24 transmits the user identity information entered by the user to IMD 16 and processor 80 of IMD 16 compares the entered user identity information to user accounts 108 as described above.

In some examples, processor 140 generates access control information as described above with respect to processor 80 of IMD 16. In such examples, where the user is an unauthenticated user, processor 140 generates access control information corresponding to general user account 124 and processor 140 applies the access control information to specify actions available to the unauthenticated user for managing information stored in memory 142. The actions available to the unauthenticated user include at least those described above. For example, the unauthenticated user may be provided with an action to clear diagnostic data 106 from programmer 24 or IMD 16 such that the diagnostic data is no longer displayed to the unauthenticated user. Other examples include actions which permit the unauthenticated user to make changes to programming, but which do not permit the unauthenticated user to synchronize those changes across the set of authenticable user accounts 122A to 122N.

The unauthenticated user may be permitted to interrogate IMD 16 and cause IMD 16 to transmit any or all of the information stored in memory 82 (FIG. 4) to memory 142 of programmer 24. After programmer 24 receives information from IMD 16, processor 140, for example, may execute computer-readable instructions which analyze the information received from IMD 16 and notify the users associated with one or more user accounts of the set of authenticable user accounts 122A to 122N if event history 112 contains one or more events. In another example, processor 140 detects that an unauthenticated user made changes to the operational parameters 102 or cleared diagnostic data 106 and, in response, notifies one or more users associated with one or more user accounts of the set of authenticable user accounts 122A to 122N.

Where the user is an authenticated user, processor 140 generates access control information corresponding to the corresponding one of the set of authenticable user accounts 122A to 122N and applies the access control information to specify actions available to the user for managing information stored in memory 142. The actions available to the authenticated user include at least those described above. For example, the authenticated user may clear diagnostic data 106 from memory 142 of programmer 24 such that no authenticated user or unauthenticated user may perform an action to display diagnostic data 106, which in some cases may include deleting the diagnostic data from memory 142. In some examples, the actions performed by authenticated and unauthenticated users on operational parameters 102, programming history 104, and diagnostic data 106 may initially modify the data stored in memory 142 of programmer 24, which may provide commands to IMD 16 to made corresponding modifications to the data stored in memory 82, e.g., via a synchronization command.

Figure 6:
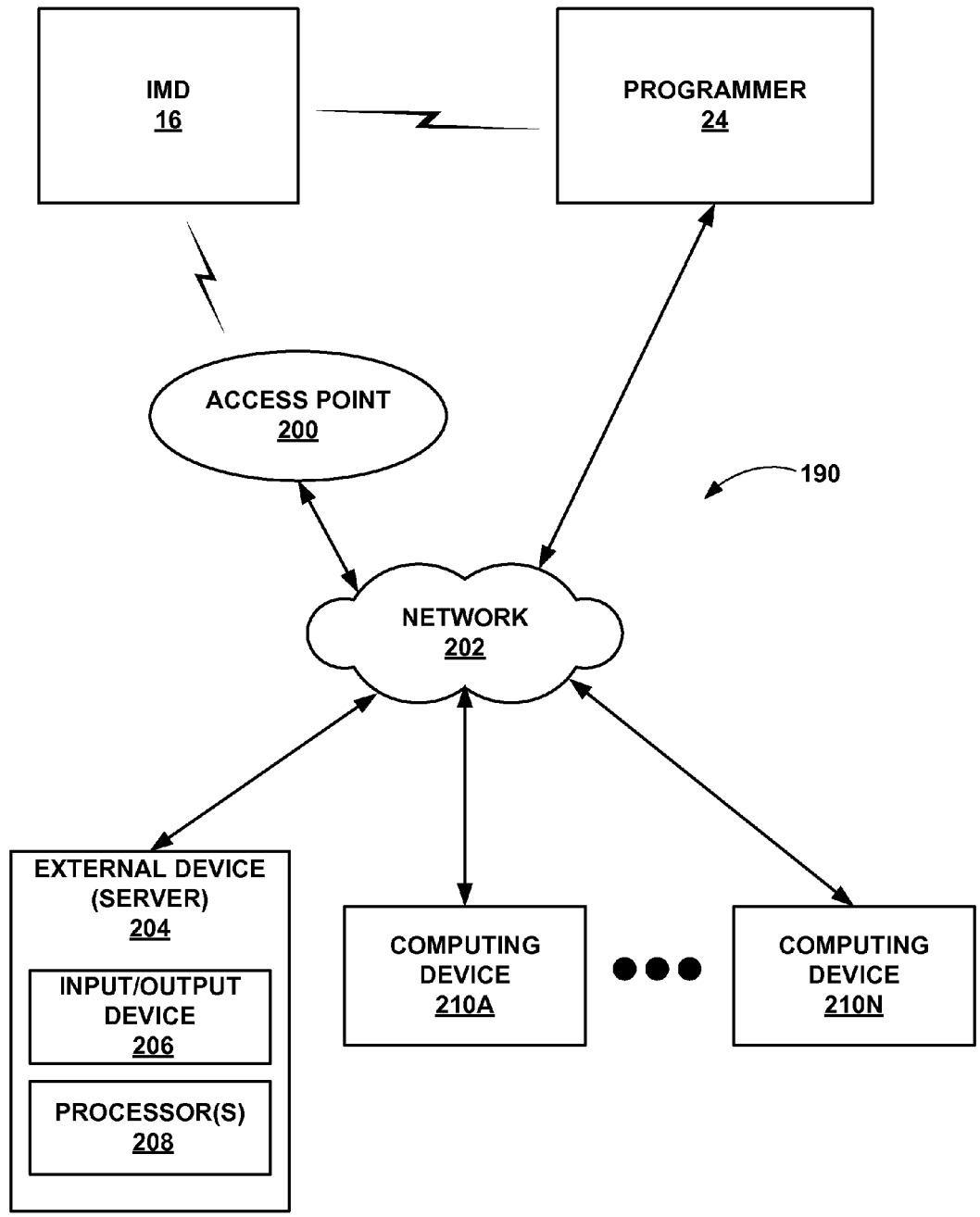
FIG. 6 is a block diagram illustrating an example system that includes an external device, such as a server, and one or more computing devices that are coupled to the IMD and programmer shown in FIG. 1 via a network.

FIG. 6 is a block diagram illustrating an example system 190 that includes an external device, such as a server 204, and one or more computing devices 210A-210N (computing devices 210), that are coupled to IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 6, access point 200, programmer 24, server 204, and computing devices 210 are interconnected, and able to communicate with each other, through network 202. In some cases, one or more of access point 200, programmer 24, server 204, and computing devices 210 may be coupled to network 202 through one or more wireless connections. IMD 16, programmer 24, server 204, and computing devices 210 may each comprise one or more processors, such as one or more microprocessors, DSPs, ASICs, FPGAs, programmable logic circuitry, or the like, that may perform various functions and operations, such as those described herein.

Access point 200 may comprise a device that connects to network 186 via any of a variety of connections, such as telephone dial-up, digital subscriber line (DSL), fiber optic, wireless, or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16.

In some examples, access point 200, server 204, or computing devices 210 may perform any of the various functions or operations described herein. For example, processor 208 of server 204 may compare user identity information received from a user to stored user account information and generate access control information corresponding to a matching user account. Processor 208 may also, upon generating the access control information, further apply the access control information to specify actions available to the user for managing stored information.

In some examples, any or all of programmer 24, access point 200, server 204, or computing device 210 may perform additional actions, such as outputting (e.g., displaying) the information associated with the user account matching the user identity information inputted by the user or actions available to the user for managing stored information.

In some cases, server 204 may be configured to provide a secure storage site for data that has been collected from IMD 16 and/or programmer 24. Network 202 may comprise a local area network, wide area network, or global network, such as the Internet. In some cases, programmer 24 or server 204 may assemble data in web pages or other documents for viewing by and trained professionals, such as clinicians, or by the patient, via viewing terminals associated with computing devices 210. Server 204 may also display the web pages or documents using input/output device 206. The illustrated system of FIG. 6 may be implemented, in some aspects, with general network technology and functionality similar to that provided by the Medtronic CareLink® Network developed by Medtronic, Inc., of Minneapolis, Minn.

Figure 7A:
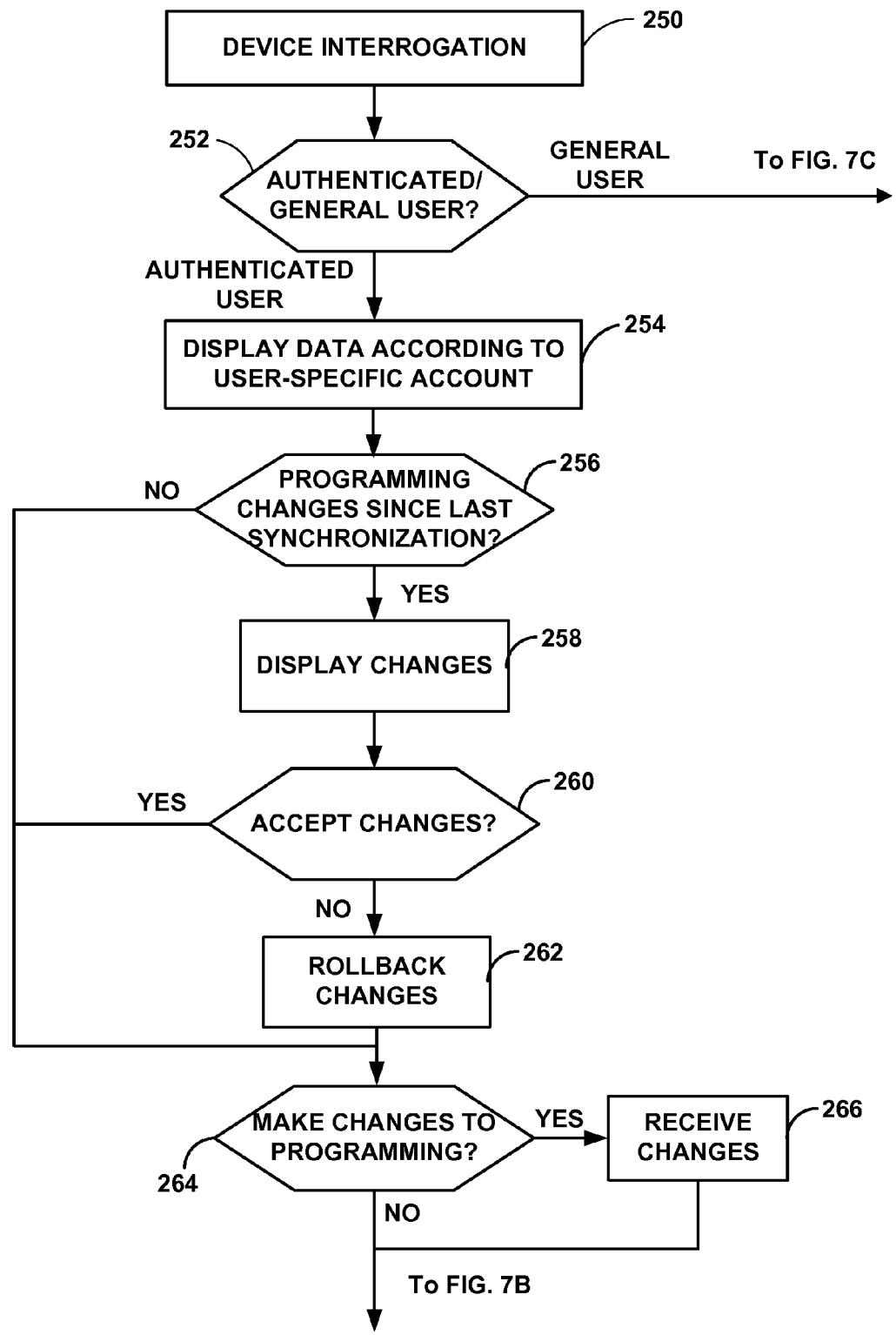
Figure 7B:
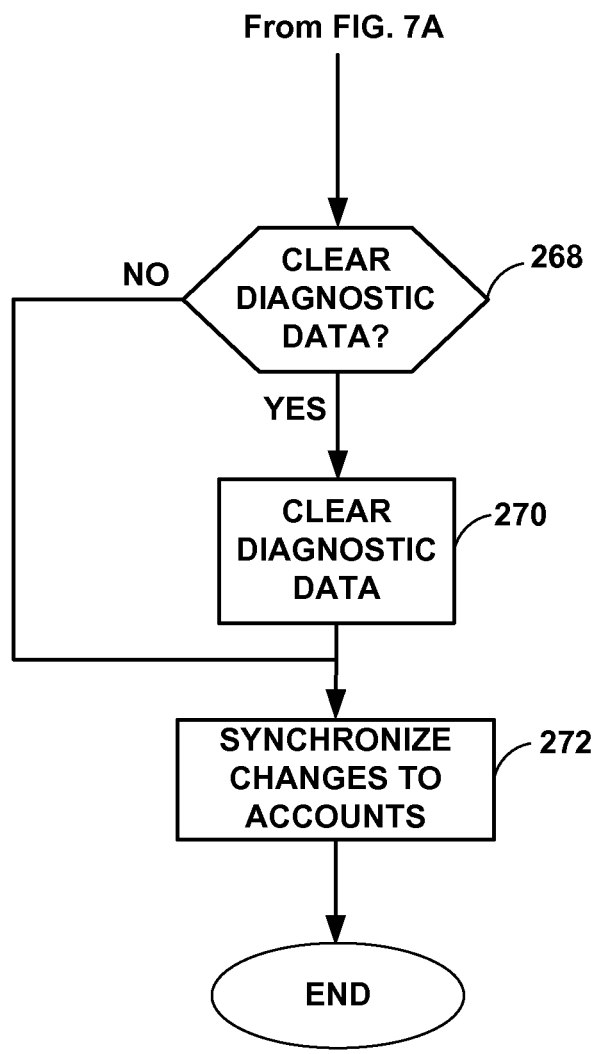

FIGS. 7A-7C are flow diagrams illustrating an example method for controlling the management of stored data via multiple user accounts. The example method may be performed by processor 80 of IMD 16, processor 140 or programmer 24, a processor of another device, such as an external server 204 or computing device 210, or any combination thereof. The information for implementing the user accounts and associated abilities to manage data, as well as the stored IMD data, may be stored in memory 82 of IMD 16, memory 142 of programmer 24, a memory of another device, such as an external server 204 or computing device 210, or any combination thereof.

In FIG. 7A, a user of a programmer 24 interrogates IMD 16 (250). A processor determines whether the user is an authenticated user or a general user (252). In some examples, the processor determines whether the user is an authenticated user or a general user based on identity information entered by the user via programmer 24. In some examples, the processor determines that the user is a general user when the user does not enter identity information. In some examples, the processor prompts the user to enter identity information when the user turns on or otherwise activates programmer 24 or interrogates IMD 14. The identity information may comprise a user name and/or password, for example.

In one example, the processor retrieves user identity information corresponding to user accounts 108. The processor compares the user-entered identity information, if any is entered, to the user identity information stored in the set of authenticable user accounts (e.g., 122A to 122N) and to the user identity information stored in general user account (e.g., 124). If the entered user identity information matches one of the set of authenticable user accounts, the user is an authenticated. If the user identity information matches general user account 124, or the user does not enter identity information, the user is an unauthenticated user, and the processor provides the functionality illustrated in FIG. 7C.

In one example, if the processor determines that the user is an authenticated user (252), the processor retrieves and/or displays diagnostic data 106, programming history, and the current operational parameters 102 of IMD 16 according to the user-specific account (254). The data retrieved and/or presented for the user may depend on when the authorized user last communicated with IMD 16, rather then the contents of the memory of IMD 16. Thus, for example, the authorized user may view changes to operational parameters 102 made by another user, such as a general user, via programming history 104, as well as diagnostic parameters 106, even if the other user cleared the programming history 104 and diagnostic data 106 when interacting with the general user account 124.

Accordingly, if another user, e.g., a general user, made changes to operational parameters 102 (256), programmer 24 displays a summary of the changes via programming history 104 (258). The authenticated user may review the changes and choose to accept the changes (260). If the user accepts the changes (260), the changes are synchronized across at least the authenticable user account associated with the authenticated user and general user account 124 and programming history 104 is updated to reflect the changes (272, FIG. 7B). In other examples, the changes may be synchronized across all of the authenticable user accounts 122A to 122N and 124. If the authenticated user rejects the changes and chooses to rollback the changes (262), operational parameters 102 are restored to the state prior to the changes made by the unauthenticated user. The rollback may be synchronized to other user accounts with programming history 104 updated to reflect the rollback (272, FIG. 7C).

The authenticated user may also elect to make changes to operational parameters 102 independent of accepting or rejecting changes made by another user (264). If the authenticated user elects to make programming changes, programmer 24 receives the changes (266). The changes may be synchronized to other user accounts with programming history 104 updated to reflect the changes (272, FIG. 7B).

Referring to FIG. 7B, the authenticated user may also review and then clear diagnostic data 106. If the authenticated user elects to clear diagnostic data 106 (268), diagnostic data 106 is cleared across at least the authenticable user account associated with the authenticated user and general user account 174 (270). In other examples discussed above, the diagnostic data may be cleared from all of the set of authenticable user accounts 122A to 122N and general user account 124. If the authenticated user elects not to clear the diagnostic data, the session may end.

If the processor that the user is a general user (252), the processor retrieves and/or displays data according to the general user account (280, FIG. 7C). For example, the processor may display the current operational parameters 102 and any diagnostic data 106 not cleared from the general account. The unauthenticated user may clear diagnostic data 106 from general user account 124, or make changes to the current operational parameters 102 (282). If the unauthenticated user chooses to clear diagnostic data 106, diagnostic data 106 is cleared from being viewed by general user account 124, but is not erased from memory 82 (284). In some examples, after diagnostic data 106 is cleared from general user account 124, the set of authenticable user accounts 122A to 122N are notified that diagnostic data 106 was cleared by the unauthenticated user (288). Notification of the authenticable user or users may be storing an indication that the data was cleared in the account 122, or by communication with a server 204 or computing device 210 via a network 202. As examples, the authenticable user may receive the notification via the user interface 144 of programmer 24 the next time the authenticable user accesses programmer 24, via an email or web account, via a cellular phone or personal digital assistant, or by fax.

If the unauthenticated user elects to make changes to the current operational parameters 102, programming history 104 is updated to reflect the changes (286). In some example, after the programming changes are recorded in the current operational parameters 102 and programming history 104 is updated (286), the set of authenticable user accounts 122 receives notification of the programming changes made by the unauthenticated user (288). Notification may be provided in any of the manners described above.

In some examples, the processor may also provide a notification to an authorized user if an event is detected by interrogation of IMD 16 by a general user or another authorized user. The event may be a clinically significant event, such as tachyarrhythmia or heart failure decompensation. The event may be occurring during interrogation, or may have occurred at any time since the notified authenticable user last interrogated IMD 16 or otherwise accessed his or her account 122. The event may be included as part of an event history 112 within diagnostic data 106. In some examples, if the processor detects that event history 112 includes events not viewed by authenticable users (282), the processor provides one or more of the set of authenticable user accounts 122 notification of the events (288). The notification of an event may include, for example, an EGM and marker channel associated with the event.

Although FIG. 7C illustrates the processor either clearing diagnostic data, receiving programming changes, or detecting an event prior to the processor ending, in some examples, the processor may perform any or all of these functions prior to the session with the general user ending. In some examples, after the authenticated or unauthenticated user has completed performing any or all of the above actions, programmer 24 may interrogate IMD 16 and store any changes made by the user to information stored in memory 142 of programmer 24 in memory 82 of IMD 16.

As described above, any of or any combination of programs 102/152, programming history 104/154, diagnostic data 106/156 and/or user accounts 108/158 may be stored in memory 82 of IMD 16 or in memory 142 of programmer 24. Any of the techniques described above may be implemented whether programs 102/152, programming history 104/154, diagnostic data 106/156 or user accounts 108/158 are stored in memory 82 of IMD 16 or in memory 142 of programmer 24. Furthermore, processor 80 of IMD or processor 140 of programmer 24 may execute any of the computer-readable instructions which cause the actions describe above to occur.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. A method comprising:
storing data of an implantable medical device and a set of user accounts in a memory, wherein the set of user accounts comprises a general user account and a plurality of authenticable user accounts;
determining whether a user that communicates with the implantable medical device via a programmer device is a general user or an authenticable user;
accessing one of the general user account or one of the plurality of authenticable user accounts based on the determination, wherein the each of the accounts includes respective access control information that specifies a respective subset of the data of the implantable medical device available and respective actions available for managing the data;
controlling access and management of the data of the implantable medical device by the user according to the access control information of the accessed one of the accounts;
during access and management of the data by an authenticable user associated with the one of the plurality of authenticable user accounts, receiving a request from the authenticable user associated with the one of the plurality of authenticable user accounts to modify one or more therapy programs stored on the implantable medical device based on data stored in a memory of the programmer device in a user account associated with the authenticable user, wherein the data was stored in the memory of the programmer device prior to when the request was received, wherein the data stored in the memory of the programmer device in the user account associated with the authenticable user defines the one or more therapy programs for controlling delivery of stimulation therapy to a patient via the implantable medical device;
in response to receiving the request from the authenticable user, modifying, based on the data stored in the memory of the programmer device in the user account associated with the authenticable user, the one or more therapy programs stored on the implantable medical device in both the general user account and the one of the plurality of authenticable user accounts associated with the authenticable user, but not in any of the other authenticable user accounts of the plurality of authenticable user accounts; and controlling the delivery of the stimulation therapy via the implantable medical device to a patient according to the one or more modified therapy programs.

2. The method of claim 1, further comprising, prior to receiving the request from the authenticable user, accessing the data stored on the memory of the programmer device.

3. The method of claim 1, further comprising, prior to receiving the request from the authenticable user, receiving, from the implantable medical device, another request for approval to modify the one or more therapy programs stored on the implantable medical device based on the data stored on the memory of the programmer device, wherein receiving the request from the authenticable user associated with the one of the plurality of authenticable user accounts to modify one or more therapy programs stored on the implantable medical device based on the data stored in the memory of the programmer device comprises receiving approval from the authenticable user associated with the one of the plurality of authenticable user accounts to modify one or more therapy programs stored on the implantable medical device based on the data stored in the memory of the programmer device.

4. The method of claim 1,
wherein determining whether the user of the programmer device that communicates with the implantable medical device via the programmer device is the general user or the authenticable user comprises:
receiving, with the programmer device, identity information for the user; and
comparing the identity information for the user to information stored in the set of user accounts, and
wherein accessing one of the general user account or one of the plurality of authenticable user accounts based on the determination comprises accessing the one of the accounts with stored identity information that matches the identity information received with the programmer device.

5. The method of claim 1,
wherein determining whether the user is the general user or the authenticable user comprises determining that the user is a general user,
wherein accessing one of the general user account or one of the plurality of authenticable user accounts comprises accessing the general user account, and
wherein controlling the access and management of the data comprises:
receiving a request from the general user accessing the general user account to clear data from the implantable medical device; and
in response to receiving the request to clear data from the general user, clearing the data from the general user account, but not from any of the plurality of authenticable user accounts.

6. The method of claim 1,
wherein determining whether the user is the general user or the authenticable user comprises determining that the user is the general user,
wherein accessing one of the general user account or one of the plurality of authenticable user accounts comprises accessing the general user account, and
wherein controlling the access and management of the data comprises:
receiving a request from the general user accessing the general user account to change a therapy program of the implantable medical device;
changing the therapy program in response to the request; and
updating a programming history accessible by the plurality of authenticable user accounts to indicate the changing of the therapy program.

7. The method of claim 1,
wherein determining whether the user is the general user or the authenticable user comprises determining whether the user is the general user or the authenticable user based upon identity information for the user, and
wherein the user is the general user if the user does not enter identity information.

8. The method of claim 1, wherein the memory comprises a memory of the implantable medical device.

9. The method of claim 1, wherein the data comprises at least one of diagnostic data or operation data of the implantable medical device.

10. A system comprising:
an implantable medical device;
a programmer device configured to communicate with the implantable medical device,
a memory configured to store data of the implantable medical device and a set of user accounts, wherein the set of user accounts comprises a general user account and a plurality of authenticable user accounts; and
a processor configured to:
determine whether a user that communicates with the implantable medical device via a programmer device is a general user or an authenticable user,
access one of the general user account or one of the plurality of authenticable user accounts based on the determination, wherein the each of the accounts includes respective access control information that specifies a respective subset of the data of the implantable medical device available and respective actions available for managing the data,
control access and management of the data of the implantable medical device by the user according to the access control information of the accessed one of the accounts,
during access and management of the data by an authenticable user associated with the one of the plurality of authenticable user accounts, receive a request from the authenticable user associated with the one of the plurality of authenticable user accounts to modify one or more therapy programs stored on the implantable medical device based on data stored in a memory of the programmer device in a user account associated with the authenticable user, wherein the data was stored in the memory of the programmer device prior to when the request was received, wherein the data stored in the memory of the programmer device in the user account associated with the authenticable user defines the one or more therapy programs for controlling the implantable medical device,
in response to receiving the request from the authenticable user, modify, based on the data stored in the memory of the programmer device in the user account associated with the authenticable user, the one or more therapy programs stored on the implantable medical device in both the general user account and the one of the plurality of authenticable user accounts associated with the authenticable user, but not in any of the other authenticable user accounts of the plurality of authenticable user accounts, and
control the delivery of the stimulation therapy via the implantable medical device to a patient according to the one or more modified therapy programs.

11. The system of claim 10, wherein, prior to receiving the request from the authenticable user, the processor is configured to access the data stored on the memory of the programmer device.

12. The system of claim 10, wherein, prior to receiving the request from the authenticable user, the processor is configured to receive, from the implantable medical device, another request for approval to modify the one or more therapy programs stored on the implantable medical device based on the data stored on the memory of the programmer device, and receive approval from the authenticable user associated with the one of the plurality of authenticable user accounts to modify one or more therapy programs stored on the implantable medical device based on the data stored in the memory of the programmer device.

13. The system of claim 10, wherein the processor is configured to:
 receive, with the programmer device, identity information for the user;
 compare the identity information for the user to information stored in the set of user accounts, and
 access the one of the accounts with stored identity information that matches the identity information received with the programmer device.

14. The system of claim 10, wherein the processor is configured to:
 determine that the user is a general user;
 access the general user account;
 receiving a request from the general user accessing the general user account to clear data from the implantable medical device; and
 in response to receiving the request to clear data from the general user, clear the data from the general user account, but not from any of the plurality of authenticable user accounts.

15. The system of claim 10, wherein the processor is configured to:
 determine that the user is the general user;
 access the general user account;
 receive a request from the general user accessing the general user account to change a therapy program of the implantable medical device;
 change the therapy program in response to the request; and
 update a programming history accessible by the plurality of authenticable user accounts to indicate the changing of the therapy program.

16. The system of claim 10, wherein the processor is configured to:
 determine whether the user is the general user or the authenticable user based upon identity information for the user, and
 determine the user is the general user if the user does not enter identity information.

17. The system of claim 10, wherein the memory comprises a memory of the implantable medical device.

18. The system of claim 10, wherein the data comprises at least one of diagnostic data or operation data of the implantable medical device.

19. A system comprising:
 means for storing data of an implantable medical device and a set of user accounts in a memory, wherein the set of user accounts comprises a general user account and a plurality of authenticable user accounts;
 means for determining whether a user that communicates with the implantable medical device via a programmer device is a general user or an authenticable user;
 means for accessing one of the general user account or one of the plurality of authenticable user accounts based on the determination, wherein the each of the accounts includes respective access control information that specifies a respective subset of the data of the implantable medical device available and respective actions available for managing the data;
 means for controlling access and management of the data of the implantable medical device by the user according to the access control information of the accessed one of the accounts;
 means for, during access and management of the data by an authenticable user associated with the one of the plurality of authenticable user accounts, receiving a request from the authenticable user associated with the one of the plurality of authenticable user accounts to modify one or more therapy programs stored on the implantable medical device based on data stored in a memory of the programmer device in a user account associated with the authenticable user, wherein the data was stored in the memory of the programmer device prior to when the request was received, wherein the data defines the one or more therapy programs for controlling delivery of stimulation therapy to a patient via the implantable medical device;
 means for, in response to receiving the request from the authenticable user, modifying, based on the data stored in the memory of the programmer device in the user account associated with the authenticable user, the one or more therapy programs stored on the implantable medical device in both the general user account and the one of the plurality of authenticable user accounts associated with the authenticable user, but not in any of the other authenticable user accounts of the plurality of authenticable user accounts; and
 means for controlling the delivery of the stimulation therapy via the implantable medical device to a patient according to the one or more modified therapy programs.

20. A non-transitory computer-readable storage medium comprising instructions that cause a programmable processor to:
 store data of an implantable medical device and a set of user accounts in a memory, wherein the set of user accounts comprises a general user account and a authenticable user accounts;
 determine whether a user that communicates with the implantable medical device via a programmer device is a general user or an authenticable user;
 access one of the general user account or one of the plurality of authenticable user accounts based on the determination, wherein the each of the accounts includes respective access control information that specifies a respective subset of the data of the implantable medical device available and respective actions available for managing the data;
 control access and management of the data of the implantable medical device by the user according to the access control information of the accessed one of the accounts;
 during access and management of the data by an authenticable user associated with the one of the plurality of authenticable user accounts, receive a request from the authenticable user associated with the one of the plurality of authenticable user accounts to modify one or more therapy programs stored on the implantable medical device based on data stored in a memory of the programmer device in a user account associated with the authenticable user, wherein the data was stored in the memory of the programmer device prior to when the request was received, wherein the data stored in the memory of the programmer device in the user account associated with the authenticable user defines the one or more therapy programs for controlling delivery of stimulation therapy to a patient via the implantable medical device; and in response to receiving the request from the authenticable user, modify, based on the data stored in the memory of the programmer device in the user account associated with the authenticable user, the one or more therapy programs stored on the implantable medical device in both the general user account and the one of the plurality of authenticable user accounts associated with the authenticable user, but not in any of the other authenticable user accounts of the plurality of authenticable user accounts; and control the delivery of the stimulation therapy via the implantable medical device to a patient according to the one or more modified therapy programs.

* * * * *